US009817012B2

(12) United States Patent
Görgen et al.

(10) Patent No.: US 9,817,012 B2
(45) Date of Patent: Nov. 14, 2017

(54) METHOD AND APPARATUS FOR A CONTROLLED DELIVERY OF PARTICLES

(71) Applicant: Bluestone Technology GmbH, Wörrstadt (DE)

(72) Inventors: Frank Görgen, Nieder-Olm (DE); Torsten Sehlinger, Undenheim (DE)

(73) Assignee: Bluestone Technology GmbH, Worrstadt (DE)

( * ) Notice: Subject to any disclaimer, the term of this patent is extended or adjusted under 35 U.S.C. 154(b) by 56 days.

(21) Appl. No.: 14/806,622

(22) Filed: Jul. 22, 2015

(65) Prior Publication Data

US 2016/0139165 A1    May 19, 2016

(30) Foreign Application Priority Data

Nov. 14, 2014   (DE) .................. 10 2014 116 694

(51) Int. Cl.
| | | |
|---|---|---|
| *G01N 35/10* | (2006.01) | |
| *A61M 15/00* | (2006.01) | |
| *B65B 9/02* | (2006.01) | |
| *B65D 75/40* | (2006.01) | |

(52) U.S. Cl.
CPC ..... *G01N 35/1009* (2013.01); *A61M 15/0065* (2013.01); *B65B 9/02* (2013.01); *B65D 75/40* (2013.01); *A61M 15/008* (2014.02); *A61M 15/0043* (2014.02); *A61M 15/0051* (2014.02); *A61M 2202/064* (2013.01); *A61M 2209/02* (2013.01); *A61M 2209/045* (2013.01)

(58) Field of Classification Search
CPC .......... G01N 35/1009; A61M 15/0065; A61M 15/0043; A61M 15/0051; A61M 15/008; A61M 2202/064; A61M 2209/02; A61M 2209/045; B65B 9/02; B65D 75/40
USPC .... 73/64.56, 863.21, 864.23, 863.81, 864.81
See application file for complete search history.

(56) References Cited

U.S. PATENT DOCUMENTS

| | | | | |
|---|---|---|---|---|
| 4,712,460 | A | 12/1987 | Allen et al. | |
| 6,012,454 | A | 1/2000 | Hodson et al. | |
| 7,765,882 | B2 * | 8/2010 | Greten | ...................... G01N 1/20 366/131 |
| 7,792,247 | B2 * | 9/2010 | Schmied | ................. A61J 3/074 378/53 |
| 7,837,942 | B2 | 11/2010 | Horak | |
| 7,868,260 | B2 * | 1/2011 | MacMichael | .......... G01G 13/06 141/83 |
| 8,118,068 | B2 * | 2/2012 | Pluvinage | ............... B01L 3/021 141/193 |
| 2001/0010224 | A1 | 8/2001 | Gonda et al. | |
| 2001/0029535 | A1 * | 10/2001 | Hirano | ................. G01N 1/2202 709/224 |

(Continued)

FOREIGN PATENT DOCUMENTS

| | | | | | |
|---|---|---|---|---|---|
| CA | 2678285 | A1 * | 12/2007 | ............... | A61B 5/08 |
| CA | 2754272 | A1 * | 9/2010 | ............... | E04H 3/08 |

(Continued)

*Primary Examiner* — Robert R Raevis
(74) *Attorney, Agent, or Firm* — Entralta P.C.; Justin G. Sanders; Peter D. Weinstein

(57) ABSTRACT

In a method and in an apparatus for the controlled delivery of particles, said particles are supplied to a measurement station in which the quantity of particles is detected. The particles are subsequently transferred by the measurement station to a dispensing device and are dispensed.

12 Claims, 2 Drawing Sheets

(56) References Cited

U.S. PATENT DOCUMENTS

Figure 1:
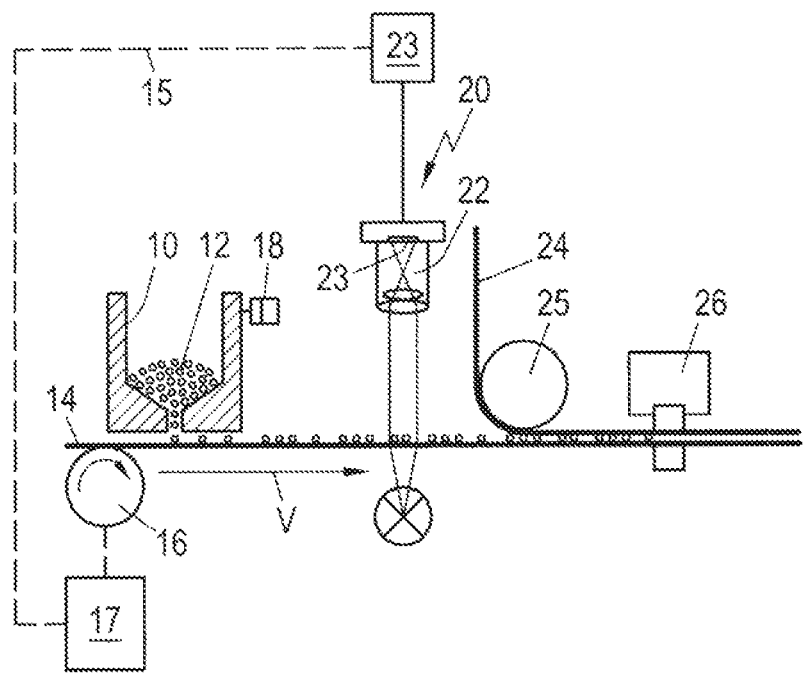

| | | |
|---|---|---|
| 2005/0258182 A1 | 11/2005 | Anderson |
| 2006/0045882 A1 | 3/2006 | Limaye |
| 2010/0068246 A1* | 3/2010 | Barlow ............... A61J 3/00 424/443 |
| 2010/0238447 A1* | 9/2010 | Hirsch ............ G01N 21/8483 356/437 |
| 2013/0270287 A1* | 10/2013 | Guo ................... G06F 17/00 221/1 |
| 2013/0330714 A1* | 12/2013 | Cooks .................. C12Q 1/04 435/5 |
| 2014/0175304 A1* | 6/2014 | Suzuki ............ G01N 15/0612 250/458.1 |

FOREIGN PATENT DOCUMENTS

| | | |
|---|---|---|
| DE | 4303256 A1 | 8/1994 |
| DE | 202008006679 U1 | 8/2009 |
| EP | 2540331 A2 | 10/2004 |
| EP | 0846009 B1 | 3/2008 |
| EP | 2210638 A1 | 7/2010 |
| WO | 9726934 A2 | 7/1997 |
| WO | 2009092520 A1 | 7/2009 |
| WO | 2010063714 A1 | 6/2010 |
| WO | 2010149123 A1 | 12/2010 |

* cited by examiner

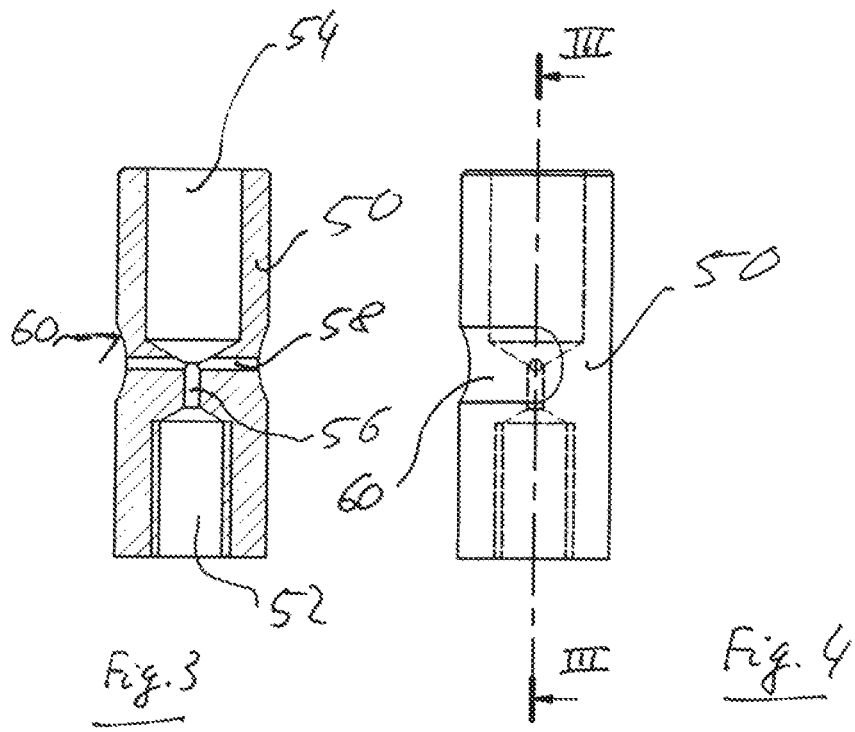
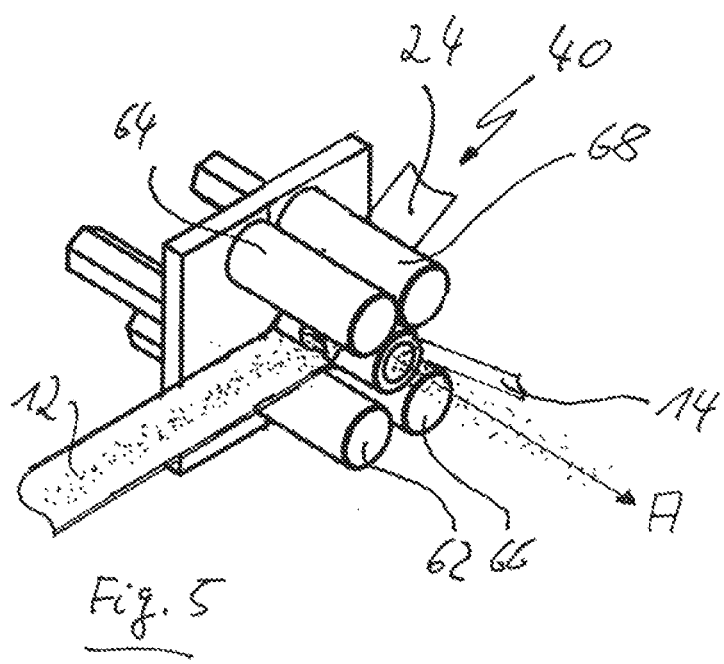

METHOD AND APPARATUS FOR A CONTROLLED DELIVERY OF PARTICLES

The present invention relates to a method and to an apparatus for a controlled delivery of allergenic particles to expose patients with allergies to a metered and controlled quantity of allergenic particles. Since the patient is exposed to different allergens in different concentrations, it is possible to discover which symptoms occur to which degree.

Various methods and apparatus for delivering allergenic particles are known from the prior art in which the delivery of the particles takes place via a turbulent air stream, which results in a discontinuous and spatially uneven distribution of the particles.

It is the object of the present invention to provide a method and an apparatus for a continuous delivery of allergenic particles with which a constant and uniform delivery of the allergenic particles can take place even at low concentrations.

This object is satisfied by the features of the independent claims.

In the method in accordance with the invention for a controlled delivery of allergenic particles, stored particles, e.g. natural and/or artificially produced particles, are first continuously supplied to a measurement station. The quantity of supplied particles is continuously detected in the measurement station so that a very precise statement can be made on how many particles are supplied in what concentration per unit of time. The detected particles are subsequently transferred from the measurement station to a dispensing device from which the particles are subsequently delivered.

What exact quantity of allergenic particles has been delivered by the dispensing device, into a space for example, can be very precisely monitored and documented using the method in accordance with the invention. Which symptoms occur to which degree can hereby be determined with a substantially higher accuracy.

Advantageous embodiments of the invention are described in the description, in the drawing and in the dependent claims.

In accordance with a first advantageous embodiment, the particles can be supplied to the measurement station in a strip-shaped arrangement. This not only facilitates the later controlled delivery of the particles, but the requirement for a simplified detection of the particles is simultaneously provided since said particles are already in a spatially limited region, namely in the strip-shaped arrangement, on entry into the measurement station.

It can furthermore be advantageous for the particles to be supplied to the measurement station in substantially one layer since an exact detection of the supplied particles is hereby facilitated.

In accordance with a further embodiment of the invention, the particles can be supplied to the measurement station in a packaging. This has the advantage, on the one hand, that the particles are also still protected from environmental influences and damage on entry into the measurement station. In addition, the particles can be more reliably detected in the measurement station if they are arranged in a packaging and are thus in a fixed position. It can also be advantageous in this respect if the particles are conducted through the measurement station in a packaging since it is hereby precluded that already detected particles are lost before a delivery by the dispensing device.

In accordance with a further advantageous embodiment, the particles can be introduced into the dispensing device in a closed packaging, with the packaging being opened in the dispensing device or only be opened in the dispensing device. It is ensured in this manner that all the particles are only released after entry into the dispensing device so that the quantity of delivered particles does not differ from the quantity of detected particles.

In accordance with a further advantageous embodiment, the particles can be supplied in a strip-shaped packaging which can in particular comprise two film strips which are preferably transparent or translucent. The particles can be continuously transported in a particularly simple manner by such a strip-shaped packaging, with a detection of the particles being able to take place in the measurement station during the transport. A detection of the particles can take place continuously during the transport without the packaging having to be opened by using a packaging having two light-permeable or radiation-permeable film strips.

In accordance with a further advantageous embodiment, the particles can be sucked off from the inner side of an open packaging in the dispensing device. It is ensured in this manner that the particles are removed from the packaging in a contact-less manner, but to a large extent. If can furthermore be advantageous if the particles are isolated by means of compressed air in the dispensing device and are delivered from the dispensing device. It is in turn provided in a contact-less manner in this way that all the particles are delivered in isolated form to release an exactly known number of particles.

It can be advantageous to achieve a particularly exact metering of the released particles if the speed at which the particles are transferred to the dispensing device is controlled, in particular regulated, in dependence on the detected quantity of particles. If the quantity of particles detected by the measurement unit per unit of time thus varies, the quantity of delivered particles can be controlled by regulating the supply speed such that said quantity is constant and corresponds to a predefined dosage.

The particles can be counted individually in the measurement station in accordance with a further advantageous embodiment. A very precise determination of the supplied quantity of particles is hereby possible.

It can furthermore be advantageous to acquire image data of the particles in the measurement station. A reliable documentation can hereby be prepared as to which particles, for example which kind of pollen, have been supplied to the patient to ensure quality control.

An apparatus in accordance with the invention for the controlled delivery of allergenic particles comprises a feed device for the continuous supply of stored particles to a measurement station in which the quantity of supplied particles is continuously detected. A dispensing device is provided for delivering the detected particles and the particles can in particular be delivered into a space by said dispensing device.

It can be advantageous with the apparatus in accordance with the invention if the measurement station has a microscope to detect the supplied particles continuously and in particular without interruption. It can in this respect, for example, be a transmitted-light microscope through which the supplied particles can be conducted. Provided that the measurement station has a counting device with which the particles supplied into the measurement station can be counted, a particularly exact detection of the supplied particles is possible. Such a counting device can be realized, for example, with the aid of an electronic camera which carries out a count of the particles conducted past the camera per unit of time via corresponding software.

In accordance with a further advantageous embodiment, the dispensing device can have an opening mechanism for opening a packaging of the particles. A packaging of the particles is hereby only opened directly before the release of the particles, whereby they are protected from environmental influences and an unwanted distribution up to the release.

The dispensing device can have a suction device which sucks off the particles from the inner side of an open packaging for the contact-less removal of the particles from the packaging It is hereby ensured that no particle remains at the inner side of the packaging in an unwanted manner so that exactly that quantity of detected particles is delivered by the dispensing device. It can be advantageous in this respect if the particles are both sucked up and delivered in isolated form by means of a nozzle arrangement in the dispensing device.

A packaging is provided in accordance with the invention for the storing and for the transport of the allergenic particles which comprises two film strips which are connected to one another and between which the allergenic particles are located in a strip-shaped arrangement. The films strips are in this respect preferably transparent or translucent so that the particles located between the film strips can be detected and can in particular be counted with the aid of an optical arrangement.

A simplified packaging can be provided in that the particles are randomly distributed in the strip-shaped arrangement in the packaging. It is hereby not necessary that the individual particles are positioned in an ordered manner in the packaging. A reliable detection and/or counting of the particles is nevertheless possible in that they are, for example, conducted through a microscope. An increased precision of the count can take place in that the particles are substantially arranged in one layer in the strip-shaped arrangement in the packaging.

In a method in accordance with the invention for manufacturing a packaging with stored allergenic particles, allergenic particles are arranged in strip shape or in linear shape between two film strips or foil strips, which are in particular transparent or translucent, whereupon the two film strips or foil strips are connected to one another at least at their margins so that the particles are enclosed between the film strips or foil strips.

Figure 2:
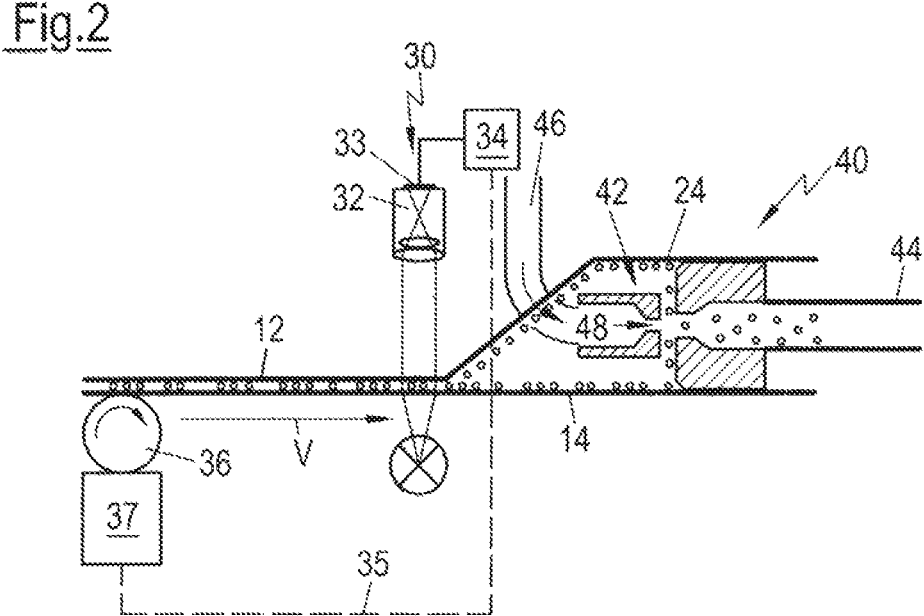

The present invention will be described in the following purely by way of example with reference to an advantageous embodiment and to the enclosed drawings. There are shown:

FIG. 1 a side view of an apparatus for manufacturing a packaging having stored particles;

FIG. 2 a side view of an apparatus for the controlled delivery of particles:

FIG. 3 a sectional view through a nozzle arrangement along the line III-III of FIG. 4;

FIG. 4 a side view of the nozzle arrangement of FIG. 3; and

FIG. 5 a dispensing device for delivering particles.

FIG. 1 shows in a highly simplified schematic representation an apparatus for manufacturing a packaging having stored particles, in particular allergenic particles, with which the particles are packed in a strip-shaped arrangement between two film strips. For this purpose, the allergenic particles 12, for example pollen, located in a reservoir 10 are delivered in a strip-shaped arrangement onto a film strip 14 which serves as a carrier and which is continuously moved via a drive device 16 in the direction of the arrow V. An outlet opening for the particles 12 through which the latter can be delivered vertically downwardly onto the film strip 14 is provided in the reservoir 10 for the delivery of the particles in a single-layer arrangement or in a substantially single-layer arrangement. To facilitate the delivery, the reservoir 10 can be provided with a vibration device and/or with a stirring device 18 to reduce the friction between the individual particles 12.

After the delivery of the particles 12 onto the film strip 14 in a continuous strip-shaped or linear arrangement, they are conducted through a counting device 20 which in the embodiment shown comprises a transmitted light microscope 22 which is provided with an electronic camera 23 which is connected to a computing device not shown in any more detail. The particles located on the film strip 14 can in this manner not only be counted, but can also be acquired in a technical imaging manner to ensure good quality control. At the same time, a control of the speed of a drive 17 of the drive apparatus 16 can take place by the counting device 20 by a closed loop via a control line 15 so that a constant number of particles is provided per unit of length of the film strip.

After passing through the counting device 20, a second film strip 24 is supplied from the upper side of the film strip 14 and is deflected into the horizontal via a deflection roller 25 so that a strip-shaped packaging having stored particles is provided by sealing the two film strips 14 and 24 in a sealing station 26 and the particles are located in a strip-shaped arrangement between the two film strips in said packaging. The two film strips which are connected to one another at their outer ends in the sealing station 26 and which are, for example, connected to one another at least at the margins by the effect of heating, by the effect of ultrasound or by adhesive are formed from a transparent material in the embodiment shown and can be wound up to form a roll after stealing for storage and for transport.

FIG. 2 shows, likewise in a highly schematic simplified representation, an apparatus for the controlled delivery of allergenic particles, comprising a feed apparatus 36 for the continuous supply of stored particles to a measurement station 30, wherein the quantity of supplied particles 12 is continuously detected in the measurement station 30. After the detection, the particles are supplied to a dispensing device 40 in which the detected particles are delivered into a space, for example.

The packaging, which is manufactured as described above and which comprises the two film strips 14 and 24 connected to one another, is conducted through the measurement station 30 in the horizontal direction along the arrow V with the aid of the feed apparatus 36 which can have a drive roll driven by a drive 37; the measurement station in turn comprises a light microscope 32 which has an electronic camera 33, with the light microscope 32 being connected to a counting device 34 in which the particles acquired by the camera 33 are photographed and individually counted. Not only a counting of the particles preferably conducted through the measurement station 30 in one layer therefore takes place in the counting device 34, but the particles are rather also photographically acquired on passing through the measurement station so that image data of the particles can be stored.

As FIG. 2 further illustrates, the counting device 34 is connected to the drive 37 of the feed apparatus 36 via a control line 35 so that the quantity of particles which leave the measurement station 30 can be kept constant by a feedback regulation in that the speed of the feed apparatus 36 is regulated in dependence on the number of particles which have been detected by the counting device 34.

After passing through the measurement station 30, the particles 12 are supplied, still in their packaging, to a dispensing device 40 by which the particles are isolated and delivered. For this purpose, the dispensing device has an opening mechanism, described in more detail in the following, for opening the packaging of the particles, with the two mutually connected film strips 14 and 24 being released from one another again by the opening mechanism. After the opening of the packaging, the particles adhering to the inner side of the packaging or to the two film strips 14 and 24 are first sucked off by a nozzle arrangement 42 and are subsequently delivered from a dispensing tube 44 in isolated form. Both the sucking of the particles from the inner side of the film strips 14 and 24 and the delivery of the particles in isolated form take place by means of compressed air which is conducted via a feed 46 into the nozzle arrangement 42 of the dispensing apparatus 40.

As FIG. 2 illustrates, the particles are sucked off from the inner side of the opened packaging or from the film strips 14 and 24, which have been separated again, with the aid of the Bernoulli effect in that the compressed air supplied through the feed 46 is conducted through a diaphragm opening 48 so that a vacuum is produced behind the diaphragm opening 48 which sucks off the individual particles from the film strips 14 and 24 and subsequently delivers them through the dispensing tube 44.

As FIG. 3 and FIG. 4 illustrate, in the embodiment shown the nozzle arrangement 42, the diaphragm opening 48 and the dispensing tube 44 are formed by a single tubular component 50 which is provided with a plurality of bores. The component 50 is generally of cylindrical shape and has a bore at its lower side, in the embodiment shown a threaded bore 52, into which a connector for the feed 46 of compressed air can be introduced or screwed. A coaxial dispensing bore 54 is introduced from the oppositely disposed side of the component 50 and the isolated particles can be delivered from the dispensing device through it. The diameters of the threaded bore 52 and of the dispensing bore 54 are substantially the same, with both bores 52 and 54 being connected to one another by a diaphragm bore 56 having a substantially smaller diameter. A suction bore 58 which has approximately the same diameter as the diaphragm bore 54 and through which the particles are sucked off in isolated form from the film strips 14 and 24 extends transversely to the diaphragm bore 56 through the component 50. A channel-like recess 60 which extends over approximately half the periphery of the component 50 is furthermore provided at the center of the component 50, at its outer jacket surface, so that the two openings of the suction bore 58 open into the channel-like recess 60.

In operation, compressed air is applied into the component 50 via the threaded bore 52 and flows out through the diaphragm bore 56 and the dispensing bore 54. A vacuum is in this respect produced in the region of the suction bore 58 and of the recess 60 with which the particles can be sucked off from the opened packagings or from the film strips 14 and 24 which have been released from one another again, which is shown in more detail in FIG. 5.

FIG. 5 shows in a perspective view the dispensing device 40 in which the two film strips 14 and 24 are supplied which are initially still connected to one another and between which the allergenic particles are located. The packaging comprising the two film strips is subsequently opened in that the lower film strip 14 and the upper film strip 24, which both extend transversely to the longitudinal extent of the component 50, loop around the component 50. The guidance takes place in the embodiment shown by a total of our guide pins 62, 64, 66 and 68 which ensure that the film strips 14 and 24 loop tightly around the component 50 and can be conducted to the wind-up apparatus after passing through the dispensing device 40 after they have been separated from one another. The inner sides of the two film strips 14 and 24 are in this respect conducted over the channel-like recess 60 of the component 50 so that all the particles located between the two film strips are acquired by the vacuum and are sucked up via the suction bore 58 and are dispensed from there via the dispensing bore 54. A delivery of the particles in isolated form in the direction of the arrow A in FIG. 5 can hereby be achieved.

The initially described method for the controlled delivery of allergenic particles can be carried out using the above-described apparatus, in which method the stored particles are continuously supplied to the measurement station 30, with the quantity of supplied particles being continuously detected in the measurement station 30. The detection can in particular take place by counting the supplied particles, with image data of the particles also being able to be acquired and stored. The supply of the particles to the measurement station preferably takes place in a strip-shaped arrangement, which is facilitated by the packaging which comprises two film strips in the embodiment shown. In the embodiment shown, the particles still located in the packaging are conducted through the measurement station 30 and are also introduced into the dispensing device 40 in the closed packaging, with the packaging only being opened in the dispensing device 40. The particles can then be sucked off from the inner side of the opened packaging in the dispensing device 40, with two film strips in this respect preferably looping around a suction device such that the particles located between the film strips are largely or almost completely sucked off from the film strip. The delivery of the particles sucked off by means of compressed air and vacuum likewise preferably takes place by means of compressed air. To ensure a constant dispensing quantity, the speed at which the particles are transferred to the dispensing device can be regulated in dependence on the detected quantity of particles. It can be advantageous for this purpose for the particles to be counted in the measurement station and for the supply feed to be regulated in dependence on the number of detected particles.

Generally any desired particles are suitable for use in the above-described method, in particular allergenic particles, for example natural or pretreated pollen. In this respect, the pollen can already be embedded in isolated form, in particular in substantially one layer, between two strips so that the detection and/or counting of the individual particles or pollen is facilitated.

The invention claimed is:

1. A method for the controlled delivery of allergenic particles, comprising the following steps:
   continuously supplying stored particles to a measurement station;
   continuously detecting the quantity of supplied particles in the measurement station;
   transferring the detected particles from the measurement station to a dispensing device; and
   delivering the transferred particles from the dispensing device, to an exposed patient to study symptoms.

2. A method in accordance with claim 1, characterized in that the particles are supplied to the measurement station in a strip-shaped arrangement.

3. A method in accordance with claim 1, characterized in that the particles are supplied to the measurement station in one layer.

4. A method in accordance with claim 1, characterized in that the particles are supplied to the measurement station in a packaging.

5. A method in accordance with claim 1, characterized in that the particles are conducted through the measurement station in a packaging.

6. A method in accordance with claim 1, characterized in that the particles are introduced into the dispensing device in a closed packaging; and in that the packaging is opened in the dispensing device.

7. A method in accordance with claim 1, characterized in that the particles are supplied in a strip-shaped packaging which in particular comprises two film strips, transparent or translucent film strips.

8. A method in accordance with claim 1, characterized in that the particles are sucked off from the inner side of an opened packaging in the dispensing device.

9. A method in accordance with claim 1, characterized in that the particles are displaced by means of compressed air in the dispensing device and are delivered from the dispensing device.

10. A method in accordance with claim 1, characterized in that the speed at which the particles are transferred to the dispensing device is controlled in dependence on the detected quantity of particles.

11. A method in accordance with claim 1, characterized in that the particles are counted in the measurement station.

12. A method in accordance with claim 1, characterized in that image data of the particles are acquired in the measurement station.

* * * * *